(12) United States Patent
Fetzer et al.

(10) Patent No.: US 8,763,462 B1
(45) Date of Patent: Jul. 1, 2014

(54) DEVICE AND METHOD FOR INSPECTING A CORNER RADIUS

(75) Inventors: Barry A. Fetzer, Renton, WA (US); Patrick Lee Anderson, Sammamish, WA (US); Hien T. Bui, Renton, WA (US); Steven Ray Walton, Wilkeson, WA (US)

(73) Assignee: The Boeing Company, Chicago, IL (US)

( * ) Notice: Subject to any disclaimer, the term of this patent is extended or adjusted under 35 U.S.C. 154(b) by 755 days.

(21) Appl. No.: 12/966,268

(22) Filed: Dec. 13, 2010

(51) Int. Cl.
*G01N 29/04* (2006.01)
*G01N 29/265* (2006.01)
*G01N 29/14* (2006.01)

(52) U.S. Cl.
USPC ............ 73/623; 73/632; 73/633; 73/865.8

(58) Field of Classification Search
CPC . G01N 29/043; G01N 29/225; G01N 29/262; G01N 2291/0231; G01N 2291/2694
USPC ................ 73/622, 623, 633, 634, 644, 865.8
See application file for complete search history.

(56) References Cited

U.S. PATENT DOCUMENTS

| | | | |
|---|---|---|---|
| 4,098,126 A * | 7/1978 | Howard | 73/865.8 |
| 4,218,923 A * | 8/1980 | Triplett et al. | 73/623 |
| 4,848,159 A | 7/1989 | Kennedy et al. | |
| 4,866,978 A * | 9/1989 | Biggerstaff | 73/865.8 |
| 5,031,458 A | 7/1991 | Young et al. | |
| 5,203,869 A | 4/1993 | Bashyam | |
| 5,343,750 A | 9/1994 | Bashyam | |
| 5,454,276 A * | 10/1995 | Wernicke | 73/865.8 |
| 5,565,633 A * | 10/1996 | Wernicke | 73/865.8 |
| 5,698,787 A | 12/1997 | Parzuchowski et al. | |
| 6,658,939 B2 | 12/2003 | Georgeson et al. | |
| 7,263,889 B2 | 9/2007 | Kennedy et al. | |
| 7,320,249 B2 | 1/2008 | Georgeson et al. | |
| 7,395,714 B2 | 7/2008 | Georgeson et al. | |
| 7,444,876 B2 | 11/2008 | Sarr et al. | |
| 7,464,596 B2 | 12/2008 | Bui et al. | |
| 7,484,413 B2 | 2/2009 | Georgeson et al. | |
| 7,617,732 B2 | 11/2009 | Bui et al. | |
| 7,690,259 B2 | 4/2010 | Bui et al. | |
| 7,836,768 B2 | 11/2010 | Young et al. | |
| 7,975,549 B2 | 7/2011 | Fetzer et al. | |
| 8,082,793 B2 | 12/2011 | Sarr et al. | |
| 8,333,115 B1 * | 12/2012 | Garvey et al. | 73/632 |

(Continued)

FOREIGN PATENT DOCUMENTS

JP 2-291961 A * 12/1990

OTHER PUBLICATIONS

Habermehl et al., "Ultrasonic Phased Array tools for Composite Inspection During Maintenance and Manufacturing," Proceedings of the 17th World Conference on Nondestructive Testing, Oct. 2008, 6 pages.

*Primary Examiner* — Daniel S Larkin
(74) *Attorney, Agent, or Firm* — Yee & Associates, P.C.

(57) ABSTRACT

A probe is used to inspect the health of a corner radius within an elongate internal cavity of a structure. The probe is transported through the cavity on a carriage that maintains the probe a substantially constant distance from the corner radius as the carriage traverses changes in the cross sectional shape of the cavity.

21 Claims, 8 Drawing Sheets

(56) References Cited

U.S. PATENT DOCUMENTS

| | | | |
|---|---|---|---|
| 8,424,385 B2 * | 4/2013 | Park et al. .................. | 73/623 |
| 2006/0053892 A1 | 3/2006 | Georgeson et al. | |
| 2006/0055399 A1 | 3/2006 | Georgeson et al. | |
| 2006/0243051 A1 | 11/2006 | Bui et al. | |
| 2008/0092672 A1 * | 4/2008 | Gibson et al. ............... | 73/865.8 |
| 2008/0314154 A1 | 12/2008 | Fetzer et al. | |
| 2009/0211361 A1 | 8/2009 | Young et al. | |
| 2010/0095775 A1 | 4/2010 | Sarr et al. | |

* cited by examiner

DEVICE AND METHOD FOR INSPECTING A CORNER RADIUS

TECHNICAL FIELD

This disclosure generally relates to inspection equipment and methods, and deals more particularly with a device and a method for inspecting a corner radius of a structure, especially composite structures.

BACKGROUND

A variety of elongated composite structures may have relatively confined internal cavities that require inspection in order to assure that the structure meets production and/or performance specifications. In some cases, these internal cavities are formed using flexible bladder tools which may cause dimensional variations greater than those that would result from using hard tooling. These larger dimensional variations make reliable inspection more difficult. For example, an ultrasonic probe may be moved along an internal wall of a structure to inspect an internal corner radius located a fixed distance from the probe. However, variations in wall thickness or angularity along length of the cavity may change the distance between the probe and the corner radius, which in turn may result in measurement error. While some features of the structure may be inspected by moving an external probe along outside walls of the structure, certain inconsistencies such as ply separations and voids slightly below the inside surface of the cavity may not be detected as desired.

Accordingly, there is a need for a method and device for inspecting composite structures having internal cavities that allow inspection from inside the cavity. There is also a need for a method and device for inspecting such structures from inside the cavity that allows a substantially constant distance to be maintained between inspection probe and the features of interest being inspected, in spite of variations in the cross sectional size or shape of the structure along its length.

SUMMARY

The disclosed embodiments provide a method and device for inspecting features of a composite structure having an internal cavity using a non-contact inspection probe. The probe is held at a substantially constant distance from the features under inspection as the probe is traversed along a surface of the structure. The embodiments allow ultrasonic inspection inside a structure in spite of variations in the cross sectional dimensions of the structure along its length. The device allows locating and traversing the probe inside an internal cavity using only two points of reference, the distance between which may change over the length of the cavity. Inconsistencies slightly below an internal surface of a relatively long structure may be reliably inspected. The embodiments also allow a curved ultrasonic array to remain aligned with a corner radius of the structure as the array is move along the length of a corner radius being inspected. The device may allow inspection of a structure from within a cavity in the structure that is otherwise substantially inaccessible from the outside.

According to one disclosed embodiment, a device is provided for inspecting a structure having an elongate internal cavity. The device comprises a carriage moveable through the cavity and an inspection probe on the carriage for inspecting the structure as the carriage moves through the cavity. The device further includes a mechanism on the carriage for maintaining a desired spacing between the inspection probe and the structure as the carriage moves through the cavity. The carriage includes first and second guides adapted to slideably engage the structure inside the cavity. The mechanism includes a slide assembly for slideably coupling the guides with each other and a device for biasing the guides to slide away from each other and into engagement with the structure. The slide assembly includes first and second telescoping slides on opposite ends of the carriage allowing the carriage to extend or retract in accordance with variations in the cross sectional shape of the cavity along its length. The device may further include a position recording device on the carriage for recording the position of the carriage along the cavity as the inspection probe inspects the radius corner, and for producing an output signal representing the recorded positions of the carriage. The position recording device may include an encoder wheel adapted to engage and roll along an outside surface of the structure. In one embodiment, the inspection probe comprises an array of ultrasonic transducers.

According to another disclosed embodiment, a device is provided for inspecting a corner radius of a structure having an elongate internal cavity with at least two opposite internal corners. The device comprises a carriage moveable through the cavity, including first and second guides respectively engaging the two opposite corners for guiding the carriage. The device further includes an inspection probe mounted on the carriage for inspecting the corner radius, and a mechanism on the carriage for adjusting the guides to maintain the fixed distance between the inspection probe and the corner radius. The mechanism further includes means for biasing the guides to move away from each other and respectively in engagement with the two corners.

According to still another embodiment, a device is provided for inspecting a corner radius within an elongate internal cavity of the structure. The device comprises an inspection probe for generating data related to the health of the corner radius, and a carriage for transporting the inspection probe through the cavity and for maintaining the inspection probe a substantially constant distance from the corner radius as the carriage traverses changes in the cross sectional shape of the cavity.

According to a further embodiment, a method is provided of inspecting a structure within an elongate cavity in a structure. The method comprises supporting a carriage within the cavity, moving the carriage through the cavity, and using a probe on the carriage to inspect features of the structure as the carriage is moved along the cavity. The method further comprises maintaining a desired spacing between the probe and the structure as the carriage moves through the cavity, by adjusting the carriage as the carriage moves through the cavity. Supporting the carriage includes supporting the carriage between diametrically opposite corners within the cavity. Supporting the carriage between the corners may include slideably engaging the opposite corners with rails on the carriage, and adjusting the carriage may include adjusting the distance between the rails. The method may further comprises sensing the position of the probe as the probe moves along the cavity, recording the sensed positions of the probe, and correlating inspection information generated by the probe with the recorded positions of the probe.

BRIEF DESCRIPTION OF THE ILLUSTRATIONS

DETAILED DESCRIPTION

Figure 1:
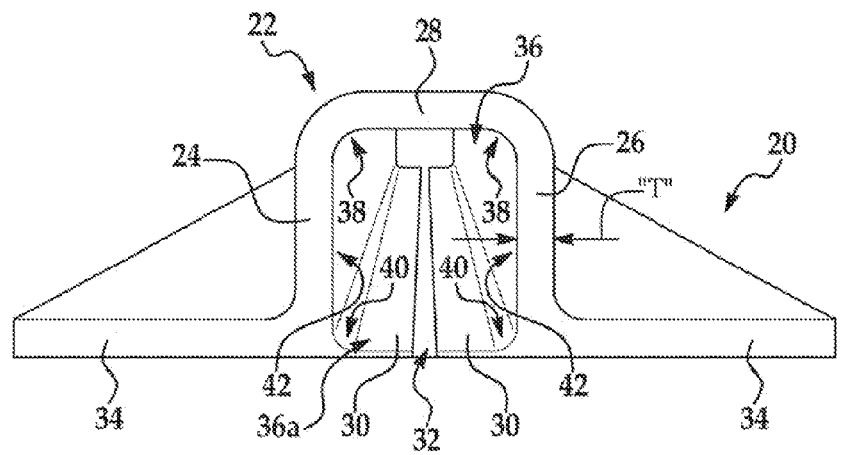
FIG. 1 is an illustration of an isometric view of a composite structure having an elongate internal cavity.
Figure 2:
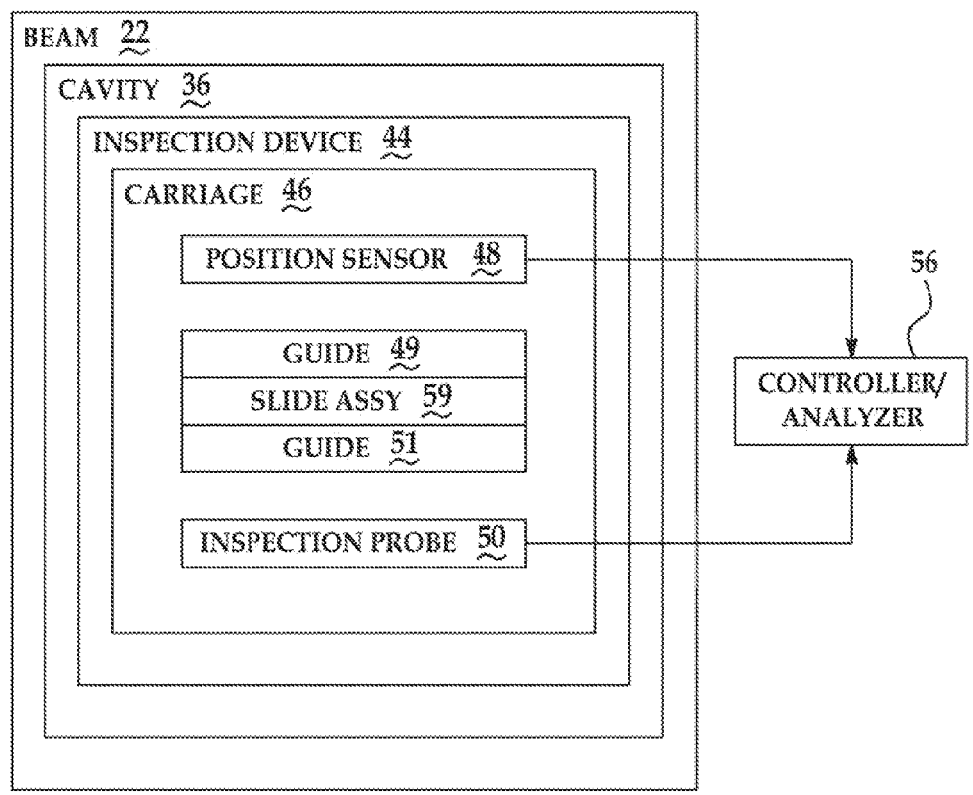
FIG. 2 is an illustration of a functional block diagram of an inspection device for inspecting the composite structure shown in FIG. 1.

Referring first to FIGS. 1 and 2, the disclosed embodiments provide a method and inspection device 44 (FIG. 2) for inspecting a composite structure 20 such as the box-like, hollow beam 22 shown in FIG. 1. The beam 22 may comprise, for example and without limitation, a stiffener or a stringer used in aerospace applications. The beam 22 includes a cap 28, side walls 24, 26 and a bottom wall 30 forming a generally rectangular, elongate cavity 36. The beam 22 further includes laterally extending flanges 34 to provide the beam 22 with additional longitudinal stiffness.

The beam 22 may be fabricated by forming fiber reinforced resin plies (not shown) over collapsible tooling (not shown) such as, without limitation, a bladder which is removed following the cure process to form the cavity 36 which has at least one open end 36a. Depending upon the particular fabrication process used to produce the beam 22, certain dimensions such as the thickness "T" of the side walls 24, 26 or cap 28 may vary along the length of the cavity 36. Similarly, the inclination of the interior surfaces 42 of the side walls 24, 26 may vary along the length of the cavity 36. Consequently, because of these dimensional variations, the cross sectional shape of the cavity 36 may vary along the length of the beam 22.

The beam 22 includes upper corner radii 38 formed between the cap 28 and the side walls 24, 26, and lower corner radii 40 formed between the bottom wall 30 and the side walls 24, 26. As used herein, "corner radii" refer to the substantially the entire thickness "T" of the beam 22 in the area of the radii 38, 40. In the particular embodiment illustrated in FIG. 1, the beam 22 includes a longitudinally extending slot 32 in the bottom wall 30. However, in other embodiments, the beam 22 may not be provided with a slot 32, in which case access to the cavity 36 is available only at the opposite ends 36a of the beam 22. In still other embodiments, the beam 22 may be closed at one end thereof, permitting access to the cavity 36 only at the other, open end 36a.

Referring particularly to FIG. 2, an inspection device 44 is used to inspect particular features of the beam 22 which may have inconsistencies that occur either during fabrication of the beam 22 or later after the beam has been placed in service. The features of interest may include, for example and without limitation, the corner radii 38, 40, the side walls 24, 26, the cap 28 and the bottom wall 30. The inspection device 44 is placed inside the cavity 36 and moved along the length of the beam 22 in order to inspect features of interest.

The inspection device 44 broadly includes a carriage 46 that is moved through the cavity 36, and an inspection probe 50 mounted on the carriage 46 which is used to perform non-contact measurements of one or more of the features of interest mentioned above. The carriage 46 includes a pair of guides 49, 51 which engage diametrically opposite pairs of the corner radii 38, 40 in order to both support and guide the carriage 46 within the cavity 36. One or more slide assemblies 59 coupled between the guides 49, 51 allow the guides 49, 51 to move toward or away from each other, and thereby accommodate changes in the cross section of the beam 22 along its length. As will be discussed below in more detail, the inspection probe 50 may comprise any of several non-contact measurement devices, including but not limited to ultrasonic transducers which generate electrical signals that can be analyzed to determine the health of particular features of the beam 22. As used herein, "health" refers to the presence or absence of a variety of inconsistencies or variations in the beam 22 along its length or may be out of tolerance for beam 22 and/or which may not conform to manufacturing specifications.

A position sensor 48 mounted on the carriage 46 senses the position of the carriage 46, and thus of the inspection probe 50, as the carriage 46 is moved through the cavity 36. Position signals generated by position sensor 48 are delivered to a controller/analyzer 56 along with inspection signals generated by the inspection probe 50. The controller analyzer 56 may comprise a programmed computer which correlates the inspection data from the inspection probe 50 with the position of the inspection probe in the cavity 36 when the data is generated.

Figure 3:
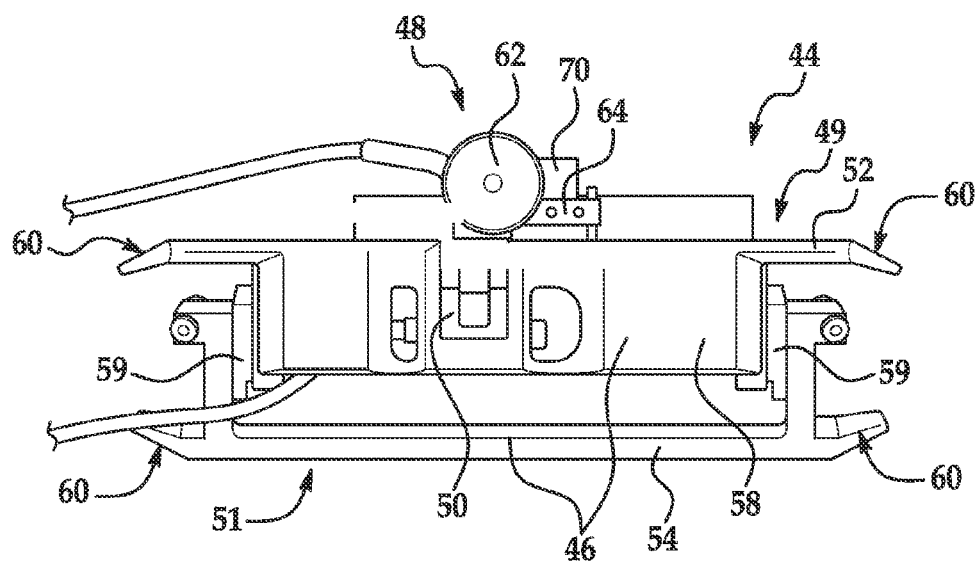
FIG. 3 is an illustration of a side view of the inspection device.

Attention is now directed to FIG. 3 which shows additional details of the inspection device 44. In the illustrated embodiment, the guides 49, 51 respectively comprise elongate, substantially continuous rails 52, 54, each having upturned or ramped and tapered extremities 60 to promote movement of the carriage 46 through the beam 22. The rails 52, 54 may have a cross section that is shaped to generally match the geometry of the radius corners 38, 40. The ramped extremities 60 help guide the rails 52, 54 into the open end 36a of the cavity 36 during insertion, and assist the rails 52, 54 in sliding over any surface imperfections in the corner radii 38, 40 (FIG. 1). The carriage 46 includes a body portion 58 secured to or formed integral with rail 52.

A suitable inspection probe 50 is mounted on the portion body 58 and is oriented to perform non-contact measurements of features of interest on the beam 22. In the illustrated embodiment, the inspection probe 50 is mounted on the body portion 58 in a position to inspect the lower corner radii 40, alternatively however the inspection probe 50 may be mounted on the body portion 58 in a position to inspect the upper corner radii 38, or in another position to inspect the side walls 24, 26. The inspection probe 50 may comprise, for example and without limitation, one or more ultrasonic transducers or an array of ultrasonic transducers that use a pulse echo technique to inspect features of interest in the beam 22, such as the corner radii 38, 40 or the side walls 24, 26. Where the corner radii 38, 40 are to be inspected, the transducers may be arranged in a curved pattern and mounted on the carriage 46 to face the particular corner radius 38, 40 to be inspected. Where one of the side walls 24, 26 is to be inspected, the transducers may be arranged in a linear array and mounted on the carriage 46 to facing and parallel to the particular side wall 24, 26 to be inspected. In still other embodiments, multiple inspection probes 50 may be mounted on the carriage 46 for simultaneously inspecting more than one feature of the beam 22. For example, both a curved sensor array and a linear sensor array may be mounted on the carriage 46 for respectively inspecting a corner radius 38, 40 and a side wall 24, 26, simultaneously, as well as the transition area (not shown) between the side wall 24, 26 and the corner radius 38, 40 being inspected. The inspection probe 50 may employ other non-contact measurement technologies to perform the inspection. The position sensor 48 may comprise an electronic encoder 70 supported on a bracket and having an encoder wheel 62 that engages the beam 22 as the carriage 46 is moved through the cavity 36 of the beam 22 (FIG. 1). A pair of slide assemblies 59 mounted on the opposite ends of rails 52, 54 for sliding movement toward and away from each other, thus allowing the carriage 46 to extend or retract, as required, to accommodate changes in the cross sectional shape of the cavity 36.

Figure 4:
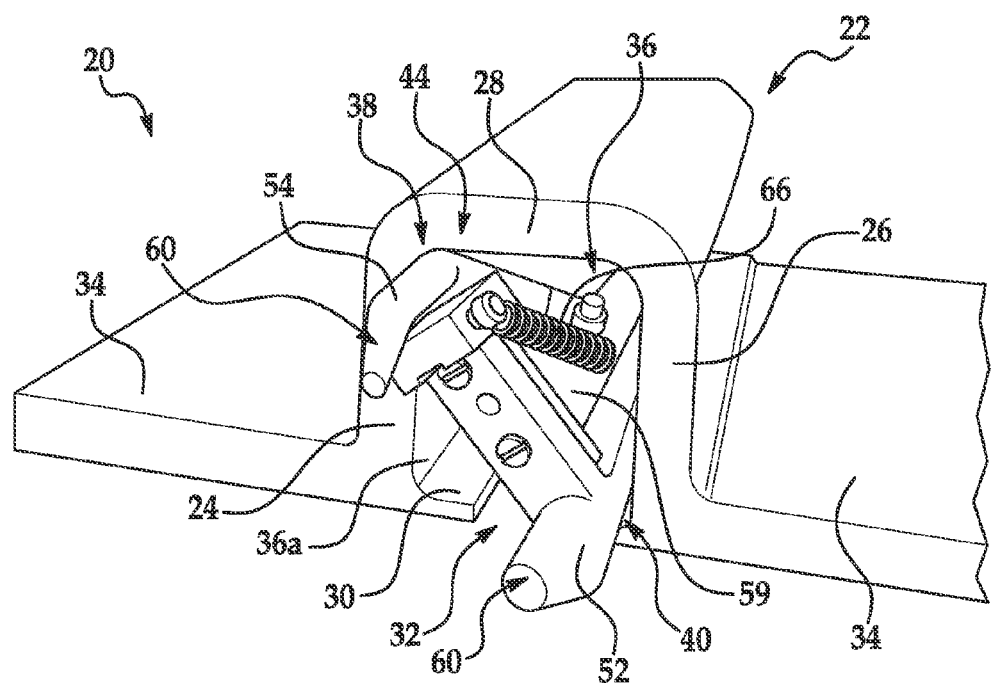
FIG. 4 is an illustration of a perspective view of an inspection device during insertion into the cavity of the composite structure shown in FIG. 1.

FIG. 4 illustrates inspection device 44 partially inserted into an open end 36a of the cavity 36 in preparation for carrying out inspection of the beam 22. Upon insertion of the inspection device 44 into the cavity 36, the rails 52, 54 engage diametrically opposite corner radii 40, 38 respectively at points along two lines inside the cavity 36 as the carriage 46 is moved through the length of the beam 22 during an inspection procedure. The rails 52, 54 both align the inspection probe 50 relative to the features to be inspected and support the carriage 46 inside the cavity 36 at only two points. Since the inspection device 44 does not contact the side walls 24,26 (FIG. 1), variations in the wall thickness "T" or the inclination of the side walls 24,26 may not substantially affect inspection data generated by the inspection probe 50. FIG. 4 also illustrates one of two springs 66 which bias the rails 52, 54 apart from each other and into engagement with the respective diametrically opposite corner radii 40, 38.

Figure 5:
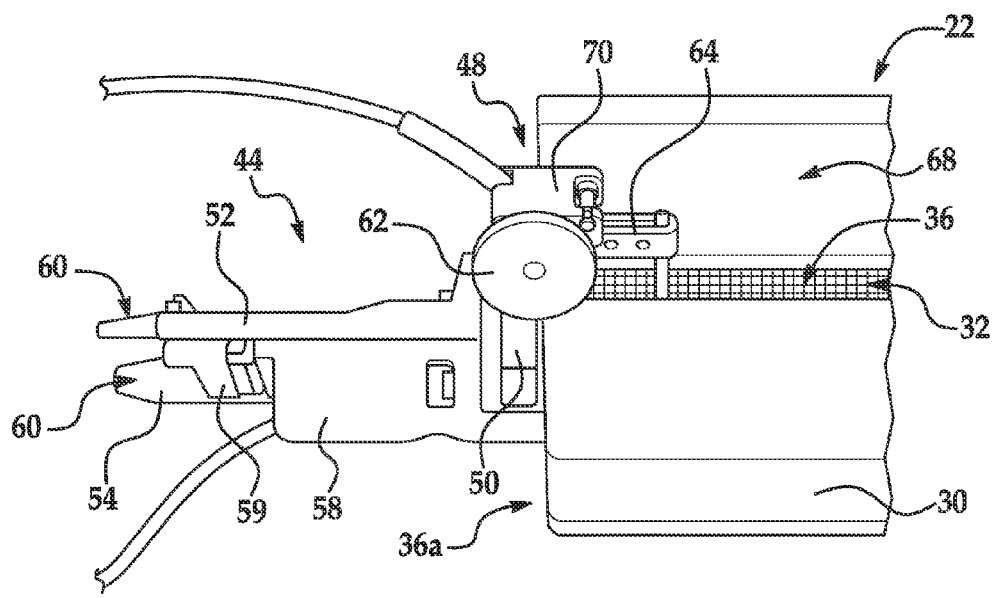
FIG. 5 is an illustration of a perspective view of the bottom of the structure shown in FIG. 1 with the inspection device partially inserted into the cavity.

FIG. 5 illustrates the inspection device 44 partially inserted into one open end 36a of the cavity 36. The position sensor 48, including the encoder 70 and encoder wheel 62, extend through the slot 32 in the bottom wall 30 of the beam 22. The encoder wheel 62 engages and rolls along the outer surface 68 of the bottom wall 30 as the carriage 46 moves through the cavity 36. Rotation of the encoder wheel 62 drives the encoder 70 which produces an electrical signal that is related to the position of the carriage 46, and thus of the inspection probe 50, along the length of the beam 22.

Figure 6:
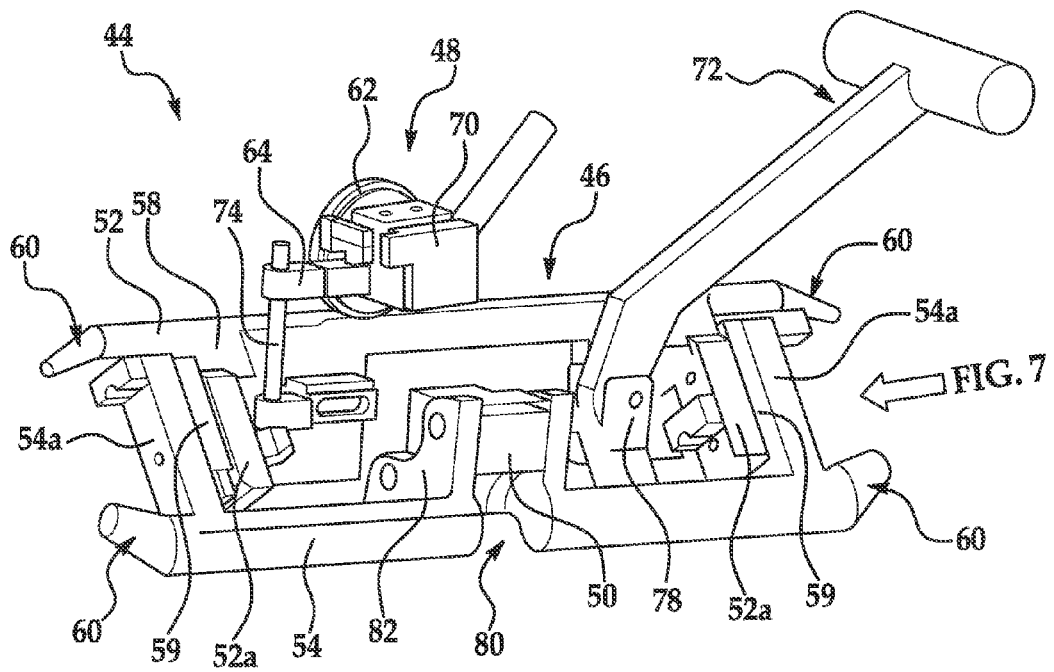
FIG. 6 is an illustration of a perspective view of another embodiment of the inspection device.
Figure 7:
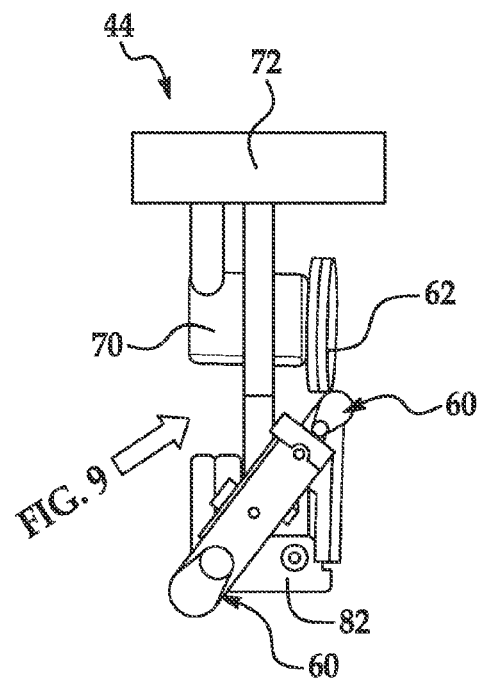
FIG. 7 is an illustration of an end view of the inspection device shown in FIG. 6.
Figure 8:
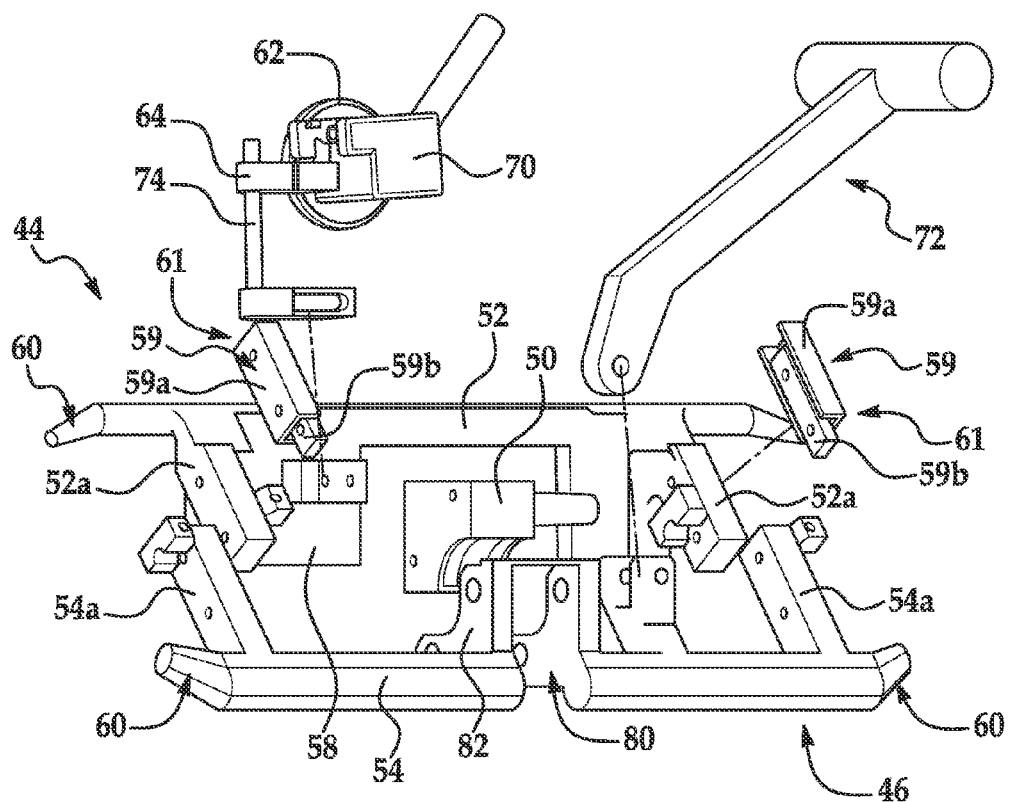
FIG. 8 is an illustration of an exploded, perspective view of the inspection device shown in FIGS. 6 and 7.

Attention is now directed to FIGS. 6, 7 and 8 which illustrate additional details of the inspection device 44. The bracket 64 supporting the position sensor 48 is mounted on a rod 74 secured to the main body portion 58 of the carriage 46. The slide assemblies 59 are coupled between overlapping legs 52a, 54a that are respectively connected to and extend inwardly from the rails 52, 54. As best seen in FIG. 8, each of the slide assemblies 59 may comprise a linear bearing 61 comprising linearly slideable, telescoping bearing numbers 59a, 59b which are respectively secured to legs 52a, 54a at opposite ends of the carriage 46. As previously mentioned, the slide assemblies 59 allow the rails 52, 54 to move away or toward each other independently, as may be required to accommodate variations in the cross sectional geometry of the cavity 36.

As best seen in FIGS. 6 and 8, a handle 72 mounted on a bracket 78 on the body portion 58 allows a technician to manually displace the carriage 46 through the cavity 36. In this example, the handle 72 extends through the slot 32 in the bottom wall 30. Another example, where the cavity 36 is completely enclosed around its sides, the carriage 46 may be moved by a rod or tether (not shown) extending through an open end 36a of the cavity 36. It may also be possible to use a motor or other automated equipment to displace the carriage 46 through the length of the cavity. As best seen in FIG. 8, in this particular embodiment, inspection probe 50 may comprise a radially arranged array of ultrasonic transducers (not shown) supported on a bracket 82 and oriented to project ultrasonic signals through a cutout 80 in rail 54.

The embodiment shown in FIGS. 6-8 is suited for inspection of the lower corner radii 40 since the inspection probe 50 is mounted on the lower rail 54. Since the lower rail 54 is always pushed against a lower corner radius 40, the inspection probe 50 remains positioned at the desired distance away from the lower corner radius 40 and this distance is maintained as the inspection device 44 is moved through the cavity 36. If the height of the cavity 36 changes for example, the two rails 52, 54 are retracted toward each other, but the inspection probe 50 maintains the same distance from the lower corner radius 40 it is inspecting.

Figure 9:
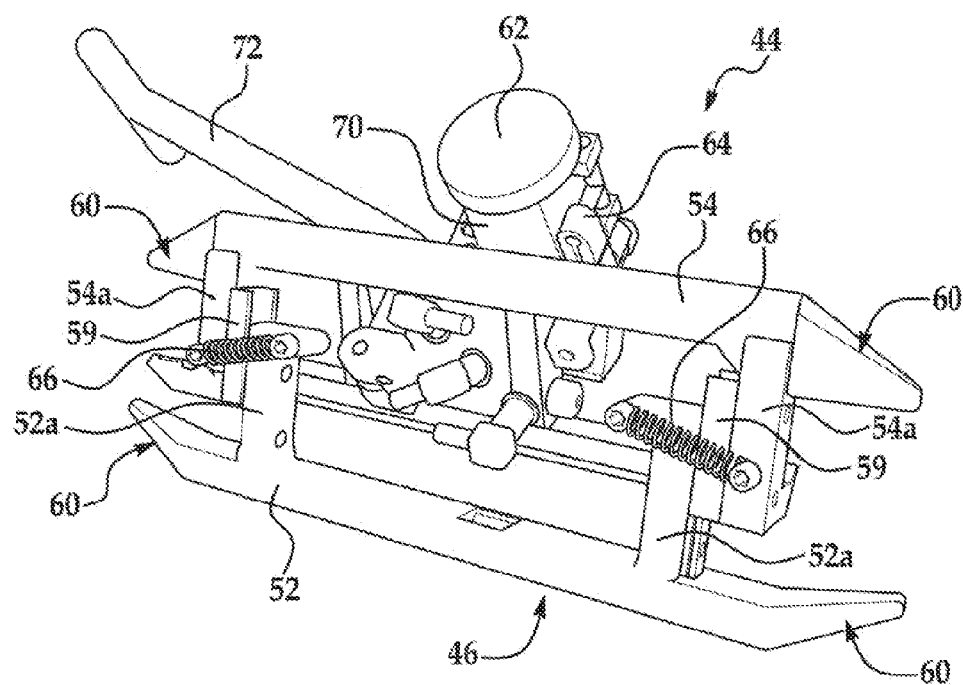
FIG. 9 is an illustration of a perspective view of a side of the inspection device shown in FIGS. 6-8.

FIG. 9 illustrates another side of the inspection device 44 shown in FIGS. 6-8. A pair of springs 66 at opposite ends of the carriage 46 bias the rails 52, 54 away from each other and into engagement with the corner radii 38, 40. In the illustrated example, the pair of springs 66 have their opposite ends connected between the legs 52a, 54a. Other devices for biasing the rails 52, 54 to slide away from each other into engagement with the corner radii 38, 40 are possible.

Figure 10:
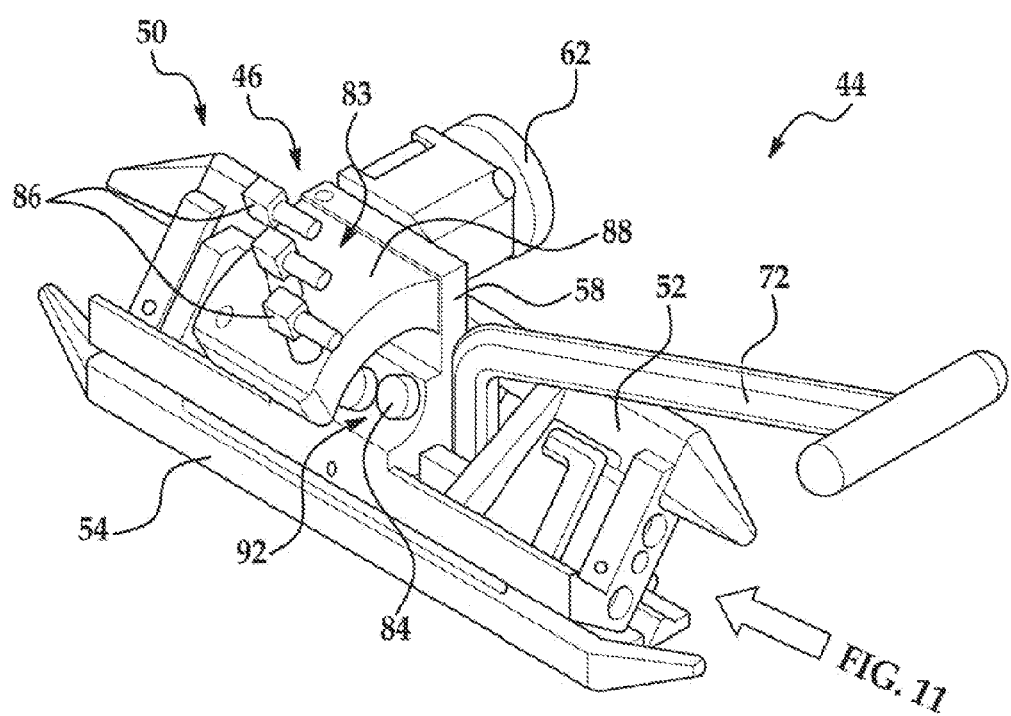
FIG. 10 is an illustration of a perspective view of another embodiment of the inspection device.
Figure 11:
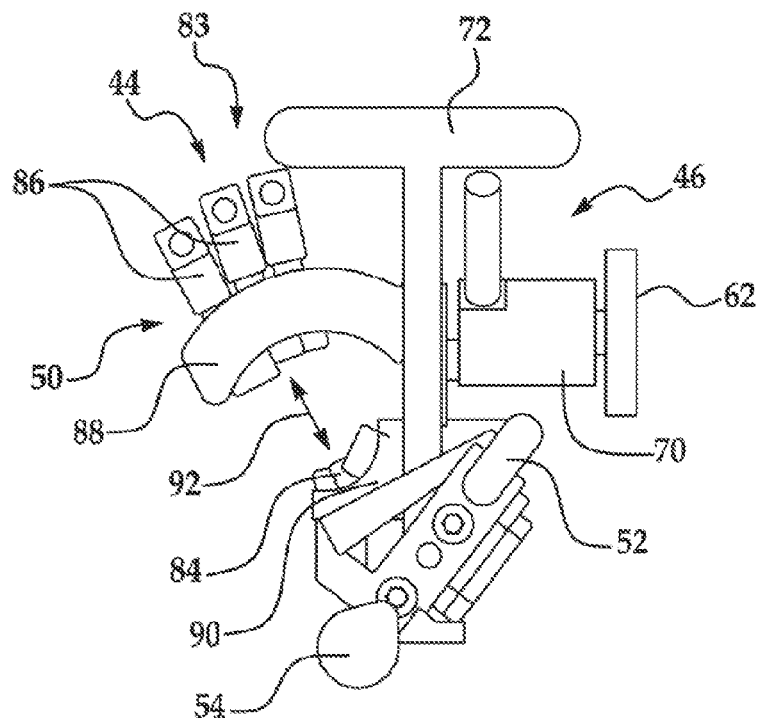
FIG. 11 is an illustration of an end view of the inspection device shown in FIG. 10.
Figure 12:
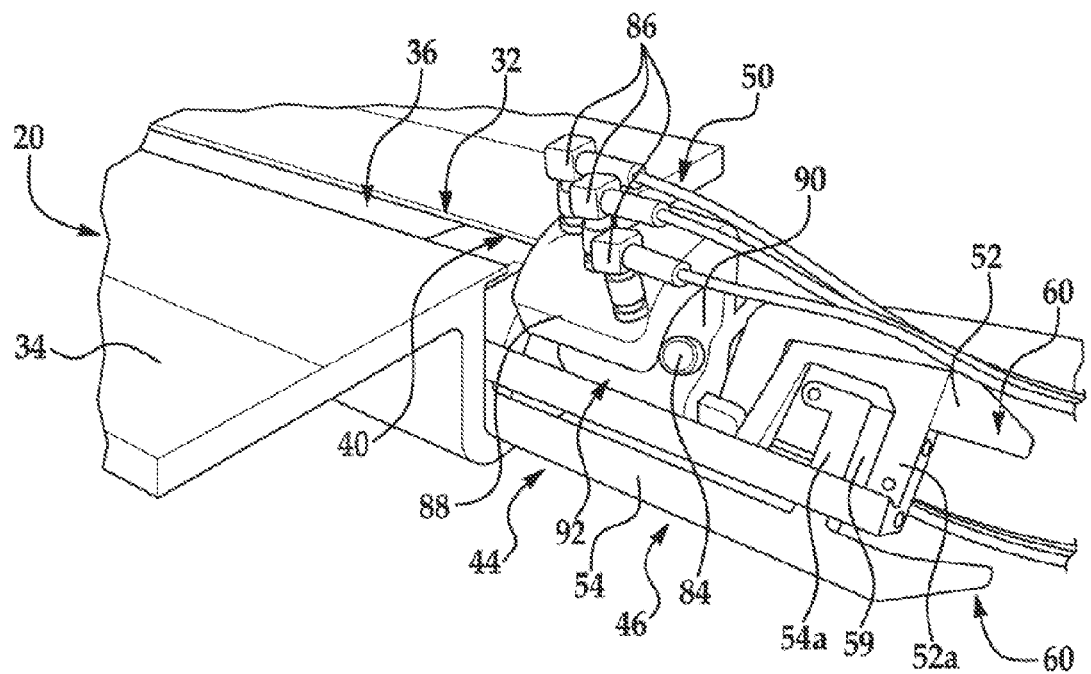
FIG. 12 is an illustration of a perspective view showing the inspection device of FIGS. 10 and 11 being inserted into the open end of the cavity in the composite structure shown in FIG. 1.

Attention is now directed to FIGS. 10-12 which illustrate another embodiment of the inspection device 44 employing a inspection probe 50 that uses a through transmission ultrasound (TTU) technique. The TTU technique may have advantages over pulse echo techniques in some applications, particularly in detecting inconsistencies near the interior surface 42 (FIG. 1) of the beam 22. The TTU technique also may require relatively little instrument setup or adjustment. The inspection device 44 shown in FIGS. 10-12 is especially useful in inspecting the lower corner radii 40 since these radii are essentially inaccessible from outside the beam 22. The inspection probe 50 comprises an array of aligned through-transmission transducer pairs 83, comprising circumferentially spaced transmitting transducers 86, and corresponding circumferentially spaced receiving transducers 86. The receiving transducers 86 are mounted on an arcuate support extending from the body portion 58. Similarly, the transmitting transducers 84 are mounted on an arcuate support 90 which also extends from the body portion 58. The transducers 84, 86 are spaced apart from each other to form a gap 92 therebetween, as best seen in FIGS. 10 and 11, and are aligned relative to each other according to Snell's Law of reflection angles.

The receiving transducers 86 are placed at an angle based on Snell's Law according to the formula:

$$\frac{V1}{V2} = \frac{\sin\alpha}{\sin\beta}$$

where V1 is sound in graphite and V2 is sound velocity in water.

Referring to FIG. 12, a perspective view of inspection device 44 is shown in use being inserted into the open end 36a of cavity 36. When the carriage 46 is placed inside the cavity 36, the transducer support 88 extends through the slot 32 such that the receiving transducers 86 are positioned outside the cavity 36 partially surrounding one of the lower corner radii 40. The transmitting transducers 84 are positioned inside the cavity 36 partially surrounding the lower corner radii 40 and are respectively aligned with corresponding ones of the receiving transducers 86. The transmitting transducers 84 are positioned to transmit ultrasonic signals normal to the inside lower corner radius 40. These signals enter the beam 22, travel through the beam 22 and exit the beam 22 where they are received by one of the receiving transducers 86.

Figure 13:
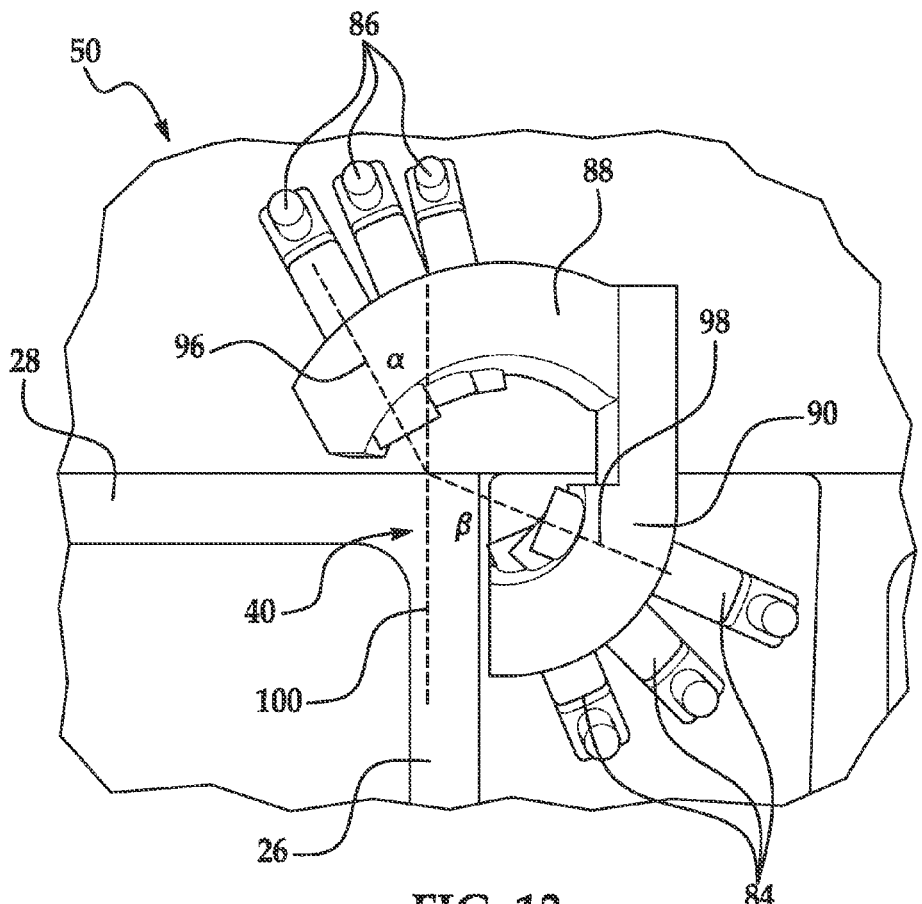
FIG. 13 is an illustration of a diagram showing a corner radius being inspected by the probe forming a part of the inspection device shown in FIGS. 10, 11 and 12.

FIG. 13 better illustrates the positions of the transmitting and receiving transducers 84, 86 respectively, relative to a lower corner radius 40 being inspected. Ultrasonic signals produced by the transmitting transducers 84 are respectively projected along a line 96 that forms an angle α relative to a vertical axis 100. The transmitted signals pass through the lower corner radius 40 and are deflected along a line 98 that forms an angle β relative to vertical axis 100 before being received by one of the receiving transducers 86. The deflection of the transmitted ultrasonic signals is in accordance with Snell's Law and may be analyzed to determine the structural health of the lower corner radius 40.

Figure 14:
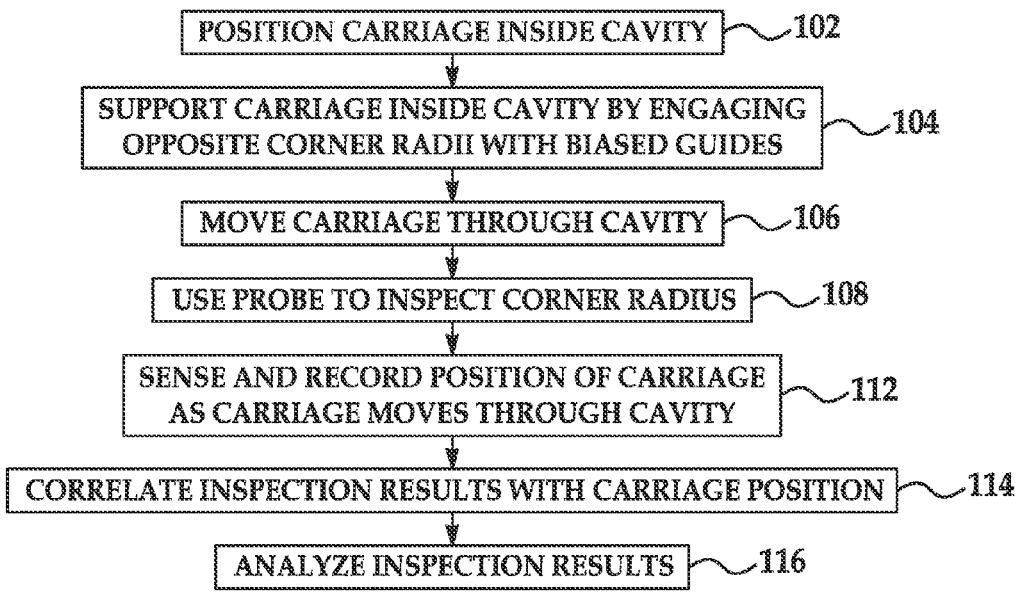
FIG. 14 is a flow diagram broadly illustrating a method of inspecting a composite structure using the inspection device.

Referring now to FIG. 14, the health of a composite structure 20, such as the beam 22 shown in FIG. 1, may be non-destructively inspected using a method that begins at step 102 with positioning the carriage 46 inside cavity 36. At step 104, the carriage 46 is supported inside the cavity 36 by using the rails 52, 54 to engage and slide along diametrically opposite corner radii 38, 40. At step 106, the carriage 46 is moved through the cavity 36 either manually or using automated means as discussed earlier. At step 108, the inspection probe 50 is used to inspect a desired corner radius 38, 40 for inconsistencies. At step 112, the position of the carriage 46 along the length of the beam 22 is sensed and recorded as the carriage 46 moves through the cavity 36. At step 114, the inspection results represented by the data generated by the inspection probe 50 is correlated with the position of the carriage 46 sensed and recorded at step 112. At step 116, the inspection results may be analyzed using a suitable controller/analyzer 56 (FIG. 2) based on inspection data that has been correlated with the position of the carriage 46 in step 114.

Figure 15:
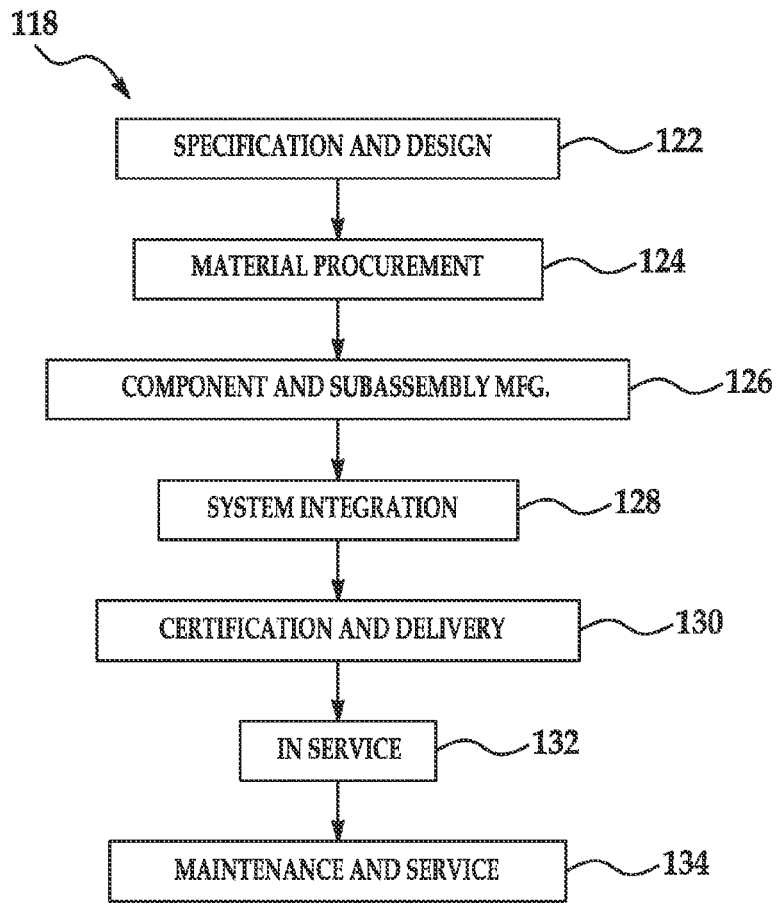
FIG. 15 is an illustration of a flow diagram of aircraft production and service methodology.
Figure 16:
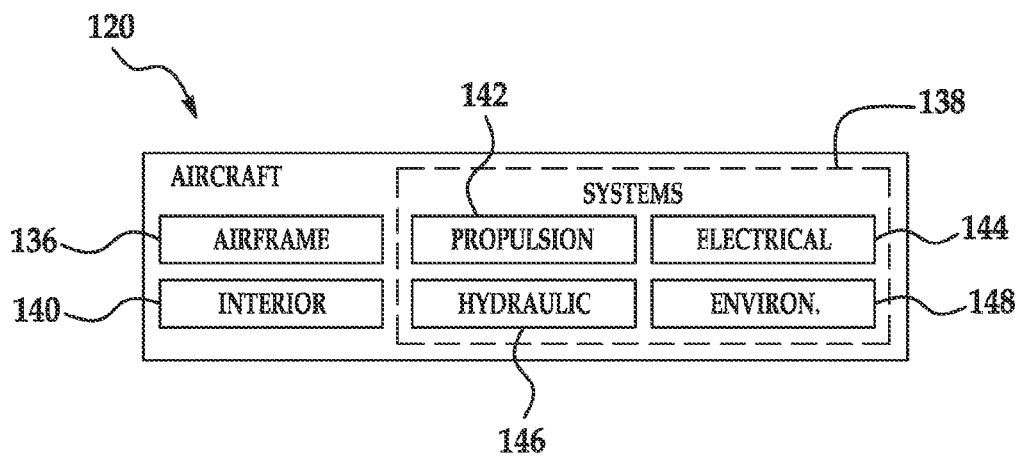
FIG. 16 is an illustration of a block diagram of an aircraft.

Referring next to FIGS. 15 and 16, embodiments of the disclosure may be used in the context of an aircraft manufacturing and service method 118 as shown in FIG. 15 and an aircraft 120 as shown in FIG. 16. During pre-production, exemplary method 118 may include specification and design 122 of the aircraft 120 and material procurement 124. During production, component and subassembly manufacturing 126 and system integration 128 of the aircraft 120 takes place. During step 126, the disclosed method and device may be employed to fabricate composite parts, such as stiffeners, which are then assembled at step 128. Thereafter, the aircraft 120 may go through certification and delivery 130 in order to be placed in service 132. While in service by a customer, the aircraft 120 may be scheduled for routine maintenance and service 134 (which may also include modification, reconfiguration, refurbishment, and so on).

Each of the processes of method 118 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 16, the aircraft 120 produced by exemplary method 118 may include an airframe 136 with a plurality of systems 138 and an interior 140. The disclosed method and apparatus may be employed to fabricate stiffeners which form part of the airframe 136. Examples of high-level systems 138 include one or more of a propulsion system 142, an electrical system 144, a hydraulic system 146 and an environmental system 148. Any number of other systems may be included. Although an aerospace example is shown, the principles of the invention may be applied to other industries, such as the automotive industry.

The apparatus embodied herein may be employed during any one or more of the stages of the production and service method 118. For example, components or subassemblies corresponding to production process 126 may be fabricated or manufactured in a manner similar to components or subassemblies produced while the aircraft 120 is in service. Also, one or more apparatus embodiments may be utilized during the production stages 126 and 128, for example, by substantially expediting assembly of or reducing the cost of an aircraft 120. Similarly, one or more apparatus embodiments may be utilized while the aircraft 118 is in service, for example and without limitation, to maintenance and service 134.

Although the embodiments of this disclosure have been described with respect to certain exemplary embodiments, it is to be understood that the specific embodiments are for purposes of illustration and not limitation, as other variations will occur to those of skill in the art.

What is claimed:

1. An inspection device for inspecting a structure having an elongate internal cavity, comprising:
   a carriage movable through the elongate internal cavity, wherein the carriage includes first and second guides adapted to slideably engage the structure inside the elongate internal cavity;
   an inspection probe mounted on the carriage for inspecting the structure as the carriage moves through the elongate internal cavity; and
   a mechanism on the carriage for maintaining a desired spacing between inspection probe and the structure as the carriage moves through the elongate internal cavity, wherein the mechanism includes a slide assembly slideably coupling the first and second guides with each other and a device for biasing the first and second guides to slide away from each other and into engagement with the structure.

2. The inspection device of claim 1, wherein the slide assembly includes first and second telescoping slides on opposite ends of the carriage allowing the carriage to extend or retract in accordance with variations in a cross section of the elongate internal cavity.

3. The inspection device of claim 1, wherein:
   the inspection probe is positioned on the carriage in spaced relationship to the structure, and
   the carriage includes a handle adapted to be gripped for moving the carriage through the elongate internal cavity.

4. The inspection device of claim 1, wherein:
   the first and second guides include elongate rails respectively positioned to engage opposite corner radii inside the elongate internal cavity, and
   the device for biasing the first and second guides includes at least one spring for biasing the elongate rails respectively into the opposite corner radii of the structure.

5. The inspection device of claim 1, wherein the inspection device further comprises:
a position recording device on the carriage for recording a position of the carriage along the elongate internal cavity as the inspection probe inspects a corner radius of the structure, and for producing an output signal representing recorded positions of the carriage.

6. The inspection device of claim 5, wherein the position recording device includes an encoder wheel adapted to engage and roll along an outside surface of the structure.

7. The inspection device of claim 1, wherein the inspection probe includes an array of ultrasonic transducers.

8. The inspection device of claim 1, wherein the inspection probe comprises a non-contact inspection probe.

9. An inspection device for inspecting a corner radius of a structure having an elongate internal cavity with at least two opposite internal corners, comprising:
a carriage movable through the elongate internal cavity, including first and second guides respectively engaging the two opposite internal corners for guiding the carriage through the elongate internal cavity;
an inspection probe mounted on the carriage for inspecting the corner radius;
a mechanism on the carriage for adjusting the first and second guides to maintain a substantially fixed distance between the inspection probe and the corner radius; and
a position recording device on the carriage for recording a position of the carriage along the elongate internal cavity as the inspection probe inspects the corner radius, and for producing an output signal representing recorded positions of the carriage.

10. The inspection device of claim 9, wherein the mechanism includes a slide coupling the first and second guides for movement toward and away from each other.

11. The inspection device of claim 9, wherein the mechanism further includes means for biasing the first and second guides to move away from each other and respectively into engagement with the two corners.

12. The inspection device of claim 9, wherein:
the first and second guides includes a pair of rails respectively adapted to engage the two opposite corners of the structure, and
the mechanism includes a spring for biasing the pair of rails into the corners.

13. The inspection device of claim 9, wherein the inspection probe comprises a non-contact inspection probe.

14. An inspection device for inspecting a corner radius within an elongate internal cavity of a structure, comprising:
an inspection probe for generating data related to a health of the corner radius;
a carriage for transporting the inspection probe though the elongate internal cavity and for maintaining the inspection probe at a substantially constant distance from the corner radius as the carriage traverses changes in a cross sectional shape of the elongate internal cavity, wherein the carriage includes guides for supporting and guiding the carriage through the elongate internal cavity, the guides including a pair of rails adapted to respectively slideably engage opposite corners of the structure within the elongate internal cavity; and
a mechanism for adjusting spacing between the pair of rails to accommodate variations in the distance between the opposite corners along a length of the elongate internal cavity, wherein the mechanism includes a linear bearing coupled between the pair of rails.

15. The inspection device of claim 14, wherein the mechanism includes at least one spring for biasing the pair of rails apart and respectively into engagement with the opposite corners.

16. The inspection device of claim 14, wherein the inspection probe comprises a non-contact inspection probe.

17. A method of inspecting a structure having an elongate internal cavity, comprising:
supporting a carriage between diametrically opposite corners within the elongate internal cavity by slideably engaging the diametrically opposite corners with rails on the carriage;
moving the carriage through the elongate internal cavity;
using a probe on the carriage to inspect features of the structure as the carriage is moved through the elongate internal cavity;
maintaining a desired spacing between the probe and the structure by adjusting a distance between the rails as the carriage moves though the elongate internal cavity;
sensing positions of the probe as the probe moves along the elongate internal cavity;
recording the sensed positions of the probe; and
correlating inspection information generated by the probe with the recorded positions of the probe.

18. The method of claim 17, wherein adjusting the distance between the rails includes biasing the rails to move apart from each other.

19. The method of claim 17, wherein the probe comprises a non-contact inspection probe.

20. A method of non-destructively inspecting a radius corner within an elongate cavity of a composite structure, comprising:
placing a carriage inside the elongate internal cavity;
supporting the carriage inside the elongate internal cavity by mounting the carriage on rails and using the rails to engage two diametrically opposite corner radii of the elongate internal cavity;
moving the carriage through the elongate internal cavity, including sliding the rails along the two diametrically opposite corner radii;
using an ultrasonic sensor on the carriage to inspect the radius corner as the carriage is moved along the elongate internal cavity and generate data indicative of a health of the radius corner;
maintaining a substantially constant distance between the sensor and the corner radius being inspected as the distance between the two diametrically opposite corner radii changes by adjusting the distance between the rails;
recording a position of the sensor as the carriage moves along the elongate internal cavity, including rolling an encoder wheel along a surface on the structure and using the encoder wheel to generate a signal related to the recorded position of the sensor; and
correlating inspection information with the data generated by the sensor.

21. A device for inspecting a corner radius within an elongate internal cavity of a composite structure, comprising:
a carriage adapted to be positioned inside the elongate internal cavity, the carriage including:
a pair of rails each having a curved cross section adapted to slideably engage a corner radius within the elongate internal cavity and having ramp-shaped extremities,
a pair of linear bearings connecting the pair of rails for sliding movement toward and away from each other, a spring connected between the pair of rails for biasing the pair of rails to move away from each other and into engagement with the corner radii, and a body connected to one of the pair of rails;

a plurality of ultrasonic transducers for sensing characteristics of the corner radius and for generating inspection signals related to the sensed characteristics, the transducers being mounted on the body and arranged in a radial array generally matching a geometry of the corner radius to be inspected;

a handle mounted on the body and adapted to be gripped for moving the carriage along the elongate internal cavity;

a position sensor for sensing positions of the carriage as the carriage moves along a length of the elongate internal cavity, the position sensor including a wheel engaging and rolling along a surface of the structure and an encoder driven by the wheel for producing position signals related to the positions of the carriage along the elongate internal cavity; and an analyzer coupled with the encoder and the transducers for analyzing a health of the structure based on the position signals and the inspection signals.

* * * * *